(12) United States Patent
Craig (10) Patent No.: US 12,208,223 B2
(45) Date of Patent: Jan. 28, 2025

(54) DEVICES, SYSTEMS AND METHODS FOR INTRALUMINAL LOCAL DRUG DELIVERY

(71) Applicant: ISOLA THERAPEUTICS, INC., Minneapolis, MN (US)

(72) Inventor: Brian H. Craig, Minneapolis, MN (US)

(73) Assignee: ISOLA THERAPEUTICS, INC., Minneapolis, MN (US)

( * ) Notice: Subject to any disclaimer, the term of this patent is extended or adjusted under 35 U.S.C. 154(b) by 565 days.

(21) Appl. No.: 16/761,692

(22) PCT Filed: Nov. 17, 2017

(86) PCT No.: PCT/US2017/062397
§ 371 (c)(1),
(2) Date: May 5, 2020

(87) PCT Pub. No.: WO2019/099036
PCT Pub. Date: May 23, 2019

(65) Prior Publication Data
US 2020/0254225 A1 Aug. 13, 2020

(51) Int. Cl.
*A61M 25/10* (2013.01)
(52) U.S. Cl.
CPC ....... *A61M 25/10* (2013.01); *A61M 2025/105* (2013.01); *A61M 2025/1052* (2013.01);
(Continued)

(58) Field of Classification Search
CPC .. A61M 2025/1052; A61M 2210/1025; A61M 2210/1035; A61M 25/1002
See application file for complete search history.

(56) References Cited

U.S. PATENT DOCUMENTS 2,210,744 A * 8/1940 Winder .............. A61M 25/1011
128/207.15
4,587,975 A * 5/1986 Salo ...................... A61B 5/0535
600/506
(Continued)

FOREIGN PATENT DOCUMENTS

CN 203264017 U 11/2013
CN 205434659 U 8/2016
(Continued)

OTHER PUBLICATIONS

International Search Report dated May 23, 2019, in PCT Appl. No. PCT/US2017/062397.
(Continued)

*Primary Examiner* — Courtney B Fredrickson
(74) *Attorney, Agent, or Firm* — MEDLER FERRO WODDHOUSE & MILLS PLLC (57) ABSTRACT

Devices, systems for localized delivery of a chemotherapy, hormonal therapy or targeted drug/biologic therapy to a target tissue area of an internal body organ of a patient. A catheter 10 forms a sealed treatment chamber in a natural lumen extending through the target tissue area. Air is purged from the chamber, which is then filled with a liquid drug solution for an adequate treatment session time, solution volume and drug concentration to saturate the target tissue area, thereby providing the treatment. The liquid drug solution may be circulated or recirculated through the chamber or maintained stationary therewithin. The drug may saturate the target tissue area and pass therethrough into the lymphatic system or interstitial space, which may serve as a reservoir of the drug for continued therapeutic treatment after withdrawal of the catheter. The chamber is evacuated at the end of the treatment session.

16 Claims, 6 Drawing Sheets

(52) U.S. Cl.
CPC . *A61M 2205/33* (2013.01); *A61M 2205/3331* (2013.01); *A61M 2210/1025* (2013.01); *A61M 2210/1035* (2013.01); *A61M 2210/1039* (2013.01)

(56) References Cited

U.S. PATENT DOCUMENTS

| | | | |
|---|---|---|---|
| 4,793,351 A | 12/1988 | Landman et al. | |
| 6,575,932 B1 | 6/2003 | O'Brien et al. | |
| 8,425,455 B2* | 4/2013 | Nentwick | A61M 1/285 604/96.01 |
| 9,233,233 B2* | 1/2016 | Pruitt | A61M 25/0017 |
| 2002/0042625 A1* | 4/2002 | Stack | A61B 17/11 606/194 |
| 2002/0111386 A1 | 8/2002 | Sekins et al. | |
| 2002/0167038 A1 | 11/2002 | Lu et al. | |
| 2003/0167038 A1* | 9/2003 | Yozu | A61M 25/1002 604/101.01 |
| 2005/0085769 A1* | 4/2005 | MacMahon | A61M 1/81 604/96.01 |
| 2006/0074399 A1* | 4/2006 | Bates | A61M 25/10 604/509 |
| 2006/0149129 A1* | 7/2006 | Watts | A61B 1/0125 600/113 |
| 2006/0167416 A1 | 7/2006 | Mathis et al. | |
| 2006/0217660 A1 | 9/2006 | Lary et al. | |
| 2007/0237739 A1 | 10/2007 | Doty | |
| 2009/0018526 A1* | 1/2009 | Power | A61M 25/10 623/1.11 |
| 2009/0192505 A1 | 7/2009 | Askew et al. | |
| 2011/0218494 A1* | 9/2011 | Gerrans | A61B 17/320725 604/101.05 |
| 2011/0245665 A1 | 10/2011 | Nentwick | |
| 2012/0136343 A1 | 5/2012 | Burnett | |
| 2012/0259215 A1 | 10/2012 | Gerrans et al. | |
| 2012/0259315 A1 | 10/2012 | Hattangadi et al. | |
| 2014/0180063 A1* | 6/2014 | Zhao | G06T 7/75 600/424 |
| 2015/0119850 A1 | 4/2015 | Seward | |
| 2015/0290438 A1 | 10/2015 | Gerrans et al. | |
| 2016/0074581 A1 | 3/2016 | Gerrans | |
| 2016/0128767 A1* | 5/2016 | Azamian | A61B 18/1492 606/41 |
| 2016/0175559 A1* | 6/2016 | Gemborys | A61M 25/1011 604/103.03 |
| 2017/0151414 A1* | 6/2017 | Albalat | A61M 25/007 |
| 2017/0348514 A1 | 12/2017 | Guyon et al. | |
| 2018/0078119 A1* | 3/2018 | Krimsky | A61B 1/00085 |
| 2018/0264247 A1 | 9/2018 | Mantri et al. | |
| 2019/0269851 A1 | 9/2019 | Panotopoulos | |
| 2019/0321332 A1 | 10/2019 | Strum et al. | |

FOREIGN PATENT DOCUMENTS

| | | |
|---|---|---|
| EP | 1693077 A2 | 8/2006 |
| EP | 2508221 A1 | 10/2012 |
| KR | 10-1085203 B1 | 11/2011 |
| WO | 2017/103105 A1 | 6/2017 |
| WO | 2017161331 A1 | 9/2017 |
| WO | 2019099036 A1 | 5/2019 |
| WO | 2020101707 A1 | 5/2020 |

OTHER PUBLICATIONS

International Search Report dated Jun. 3, 2021 in PCT Appl. No. PCT/US2021/015004.

The International Search Report and the Written Opinion of the International Searching Authority issue dated Aug. 22, 2019 in international Application No. PCT/US2018/061607.

Lee et al., "The potential to treat lung cancer via inhalation of repurposed drugs," Advanced Drug Delivery Reviews 133:107-130 (2018).

Xie et al., "Pulmonary delivery of cisplatin-hyaluronan conjugates via endotracheal instillation for the treatment of lung cancer," International Journal of Pharmaceutics 392(1-2):156-63 (2010).

* cited by examiner

DEVICES, SYSTEMS AND METHODS FOR INTRALUMINAL LOCAL DRUG DELIVERY

CROSS-REFERENCE TO RELATED APPLICATIONS

This application is a national phase entry under 35 U.S.C. 371 of International Application No. PCT/US2017/062397, filed Nov. 17, 2017, the entire content of which is incorporated by reference herein.

TECHNICAL FIELD

The present disclosure relates to methods for delivery of a drug to a target tissue area of an internal body organ of a patient and, more particularly, relates to intraluminal catheters and methods for treatment of cancer and other diseases by localized chemotherapy, hormonal therapy or targeted drug/biologic therapy.

BACKGROUND

Nearly all chemotherapeutics are systemic, which creates the following limitations:
  Toxicity: Systemic toxicity can create issues that result in restricting therapeutic dosing and are associated with a range of adverse effects that are either life threatening, e.g. immunosuppression, neutropenic enterocolitis, gastrointestinal distress, tumor lysis syndrome, organ damage, or are lifestyle limiting, e.g. anemia, fatigue, nausea/vomiting, hair loss, infertility, teratogenicity, peripheral neuropathy, cognitive impairment, potentially making chemotherapy dangerous or at least stressful to the body.
  Repeat Dosing: Most chemotherapeutics are delivered intravenously (IV) but some can be delivered orally, which requires they must be prepared in a way that allows the drug to survive stomach acid while being able to be absorbed in the intestines. Most require multiple doses, which require ongoing risk to potential adverse events and patient compliance to dosing regimens.

BRIEF DESCRIPTION OF THE DRAWINGS

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

Specific embodiments of the present invention are now described with reference to the figures, wherein like reference numbers indicate identical or functionally similar elements. The terms "distal" and "proximal" are used in the following description with respect to a position or direction relative to the treating operator. "Distal" or "distally" are a position distant from or in a direction away from the operator. "Proximal" and "proximally" are a position near or in a direction toward the operator. The term "target," as in "target tissue, target area, target organ, or target region" is used to refer to diseased tissue of a hollow organ and/or tissue of a natural tract or lumen extending therethrough.

The following detailed description is merely exemplary in nature and is not intended to limit the invention or the application and uses of the invention. Platforms and methods of this disclosure may reduce the limitations of systemic drug delivery. A highly localized method of chemotherapy may reduce complications and increase effectiveness for inductive (curative), neoadjuvant (prior to surgery), or adjuvant (after surgery) drug treatments. Such a treatment may be localized to hollow organ or natural lumens. A selected drug can be delivered in liquid, aerosol/nebulizer, or even sprayed. The hollow organ is locally bathed in the drug to achieve drug absorption into the targeted organ tissue. Although the description of embodiments hereof is in the context of treatments performed within a variety of natural hollow body lumens or tracts, the invention may also be used in any other body passageways or in extraluminal locations where it is deemed useful. Furthermore, there is no intention to be bound by any expressed or implied theory presented in the preceding technical field, background, brief summary or the following detailed description.

Figure 1:
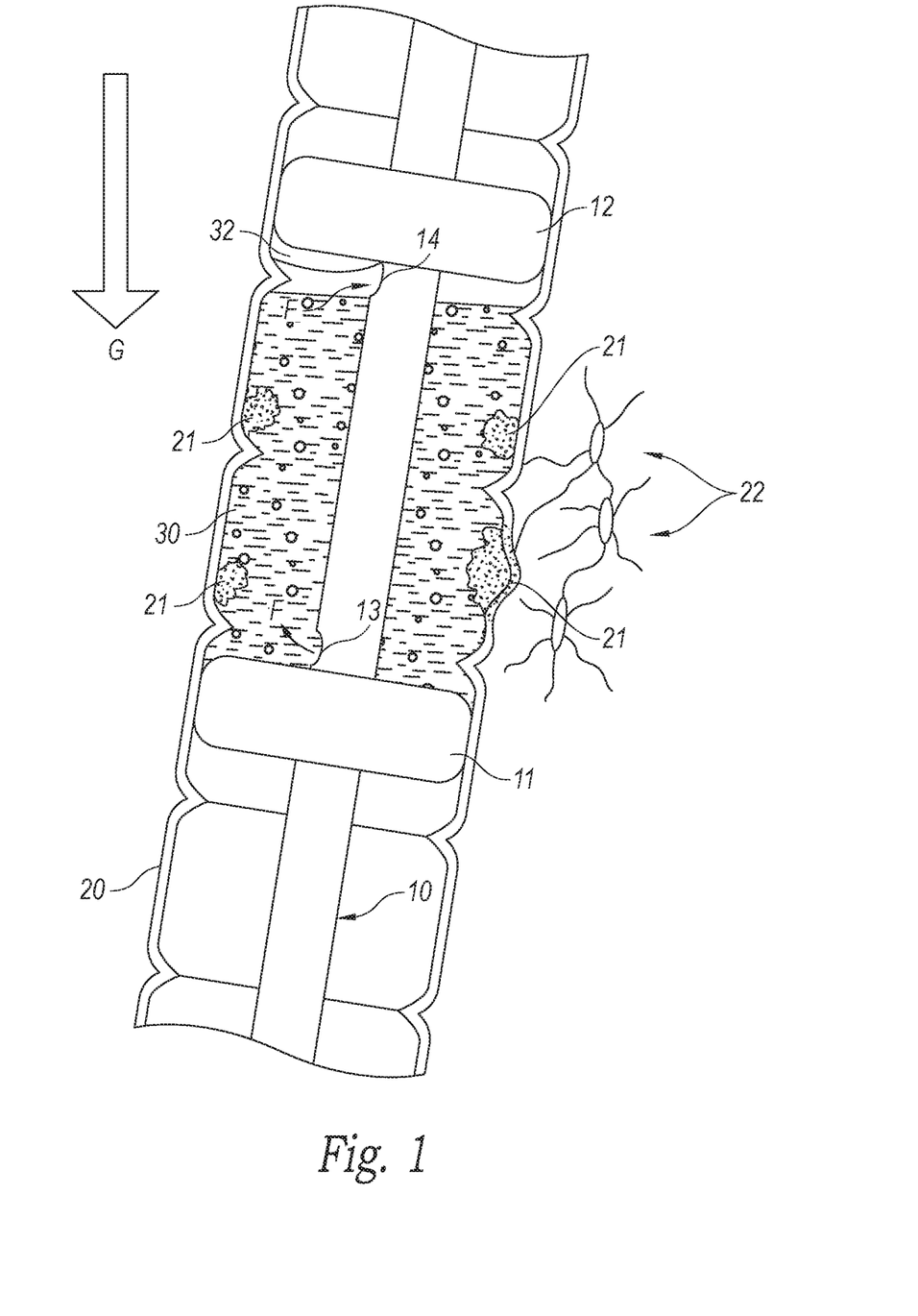
FIG. 1 illustrates a chemotherapeutic treatment of a portion of an intestine using a catheter in accordance with an embodiment of the disclosure.
Figure 6:
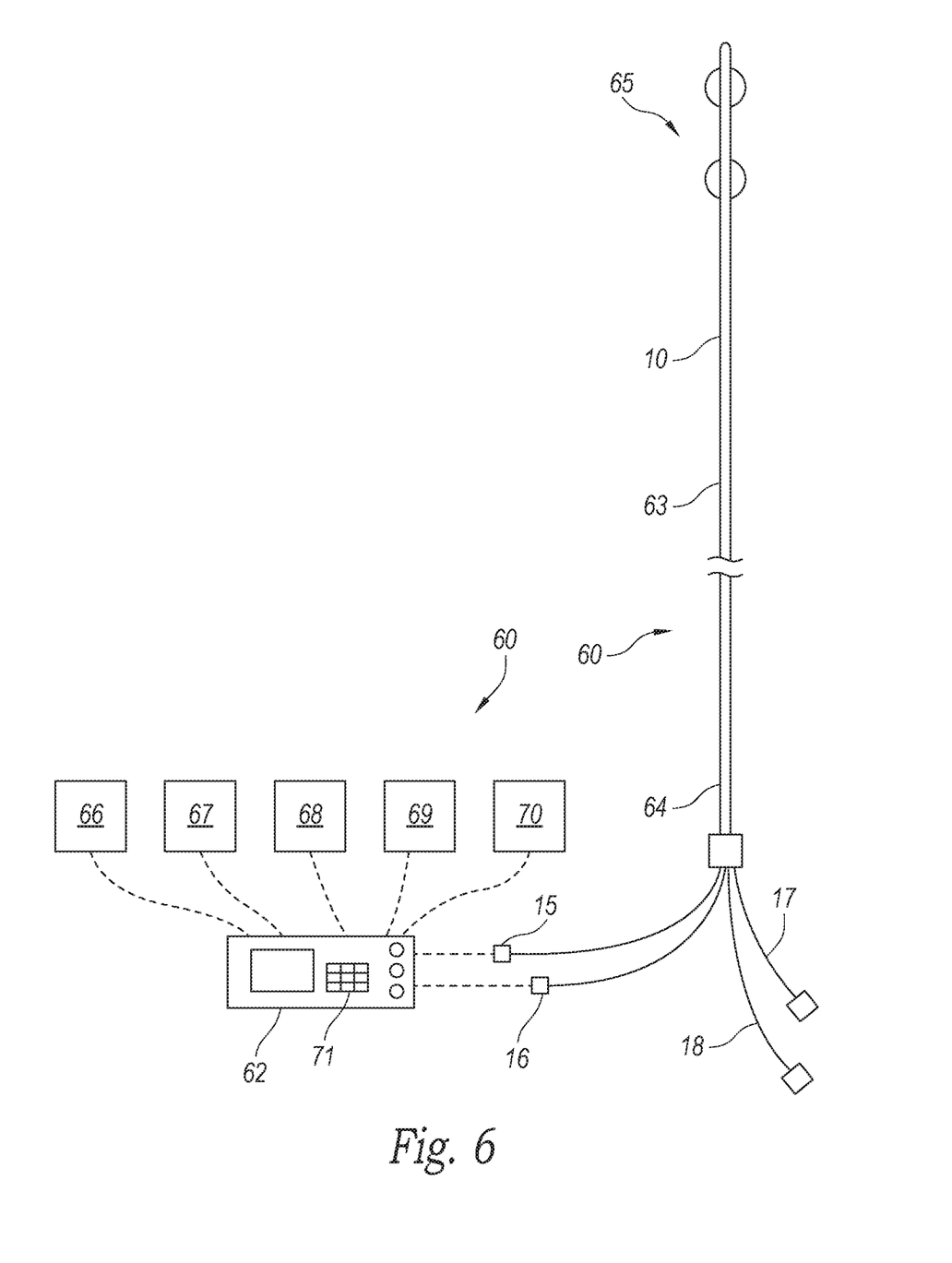
FIG. 6 is a schematic view of a treatment system in accordance with the disclosure.

FIG. 1 illustrates a catheter 10 configured in accordance with an embodiment of the present technology. Catheter 10 having an elongate flexible shaft is shown in a deployed configuration within a target region of a natural lumen, which in this example is a portion of a large intestine or colon 20. Expandable members 11, 12 are mounted about a distal region of catheter 10, and are longitudinally spaced apart such that, when expanded into sealing contact with the inner wall of colon 20, a closed treatment chamber is defined between expandable members 11, 12 and the intestinal wall. The treatment chamber may be considered to be an annular chamber because of the annular cylinder formed between the catheter shaft and the natural lumen. Herein, "closed" means the treatment chamber is excluded from fluid communication with other parts of the natural lumen beyond the expandable members. An expandable member for the present technology may be a mechanically operated sealing element or a balloon that is inflatable with a fluid that may be either a gas or a liquid. In the illustrated embodiment, the treatment chamber includes one or more polyps or other cancers 21. Catheter 10 is reversible, meaning that the flexible catheter shaft may be considered to extend proximally either upward or downward in FIG. 1. Ports 13, 14 fluidly communicate the treatment chamber with respective lumens (not shown) that extend proximally through the catheter to terminate at respective connectors 15, 16 located at the proximal end thereof, as shown in FIG. 6.

Figure 4:
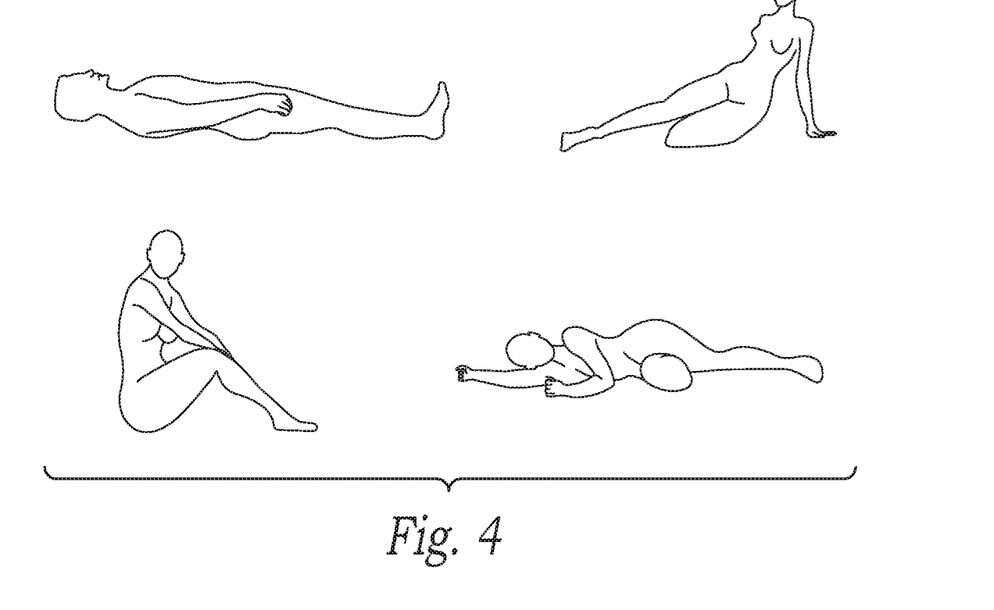
FIG. 4 shows several exemplary positions a patient may assume during a treatment procedure in accordance with the disclosure.

Once catheter 10 has been deployed as shown in FIG. 1, the operator may assess the orientation of the treatment chamber with respect to gravity G, and may reposition the patient, if necessary, to orient the treatment chamber as close to vertical as possible in order to facilitate air evacuation as the chamber is filled with liquid. The avoidance of air bubbles or air pockets may ensure that all of the inner wall of colon 20 in the treatment chamber is bathed in liquid drug solution 30. FIG. 4 shows examples of different patient positions that may provide a vertical treatment chamber. In the embodiment illustrated in FIG. 1, the portion of colon 20 enclosing the treatment chamber is nearly vertical with port 14 being located at a high point in the chamber. Because catheter 10 is reversible, the patient or the catheter could be positioned such that port 13 is located at a high point in the chamber (not shown). It is the operator's choice how to position or repositioning the patient, based on comfort of the patient and convenience of the operator and as a result, either of ports 13, 14 may become the upper port in the treatment chamber. The upper port may be defined as the egress port and the other, lower port may then be defined as the ingress port. Once the treatment chamber, catheter lumens, extension lines (if used), and pump are purged of air as described below, the patient may be repositioned or returned to a position that may be more comfortable for the patient and/or more convenient for the operator.

After the treatment chamber is oriented with respect to gravity, a liquid drug solution 30 is admitted or pumped into the chamber via the ingress port, i.e. port 13 in FIG. 1. As liquid drug solution 30 fills the treatment chamber from bottom to top, air is purged from the chamber via the egress port, i.e. port 14 until the liquid drug solution reaches port 14. See flow arrows F in FIG. 1. Optionally, partial vacuum may be applied to egress port 14 to assist or hasten the purging process. In this way, the treatment chamber is filled with liquid drug solution 30, leaving only a small air bubble 32, or preferably no air bubble at all. After the treatment chamber is filled with liquid drug solution 30, air may also be purged from all catheter lumens, extension lines (if used), and a circulating pump such as pump 67 described below to form a closed fluid circuit that may be a closed-loop fluid circuit.

In an alternative purging method, after the treatment chamber is oriented with respect to gravity, a liquid such as sterile saline is pushed into the chamber via the ingress port, i.e. port 13 in FIG. 1. As saline fills the treatment chamber from bottom to top, air is purged from the chamber via the egress port, i.e. port 14 until the saline reaches port 14. See flow arrows F in FIG. 1. After the treatment chamber is filled with saline, air may also be purged from all catheter lumens, extension lines (if used), and a circulating pump such as pump 67 described below to form a closed fluid circuit that may be a closed-loop fluid circuit. The saline in the fluid circuit can then be replaced with liquid drug solution 30.

Once the closed fluid circuit is purged of air and filled with liquid drug solution 30, a treatment session may then be conducted by circulating the liquid drug through the closed fluid circuit to maintain a homogeneous concentration of the drug throughout the treatment chamber. Herein, "circulating" means causing a fixed volume of liquid drug solution 30 to flow through the closed fluid circuit between first and second external reservoirs, e.g. first and second syringes connected to respective ports 15, 16 shown in FIG. 6, without intentional loss of the liquid solution either inside or outside of the patient. The circulating flow of liquid drug solution 30 may be unidirectional during the treatment session or may reverse direction one or more times between the first and second reservoirs. Pushing or filling a liquid, either a drug solution or saline, from a first graduated syringe through the closed fluid circuit and into a second graduated syringe allows the operator to initially confirm and subsequently monitor seal integrity of the treatment chamber by comparing input and output volumes.

Alternatively, ports 15, 16 may be connected to input and output ports of a pump thereby forming a closed-loop fluid circuit. Herein, a "closed-loop fluid circuit" is considered to be a subset of closed fluid circuits. In this arrangement, a treatment session may be conducted by recirculating the liquid drug solution 30 through the closed-loop fluid circuit to maintain a homogeneous concentration of the drug throughout the treatment chamber. Herein, "recirculating" is considered to be a subset of "circulating," and means causing liquid drug solution 30 to continuously flow, e.g. via pump 67 shown in FIG. 6 through a closed-loop fluid circuit without intentional loss of the liquid solution either inside or outside of the patient.

To conduct chemotherapy safely and effectively in accordance with an embodiment of the present technology, it may be useful to predetermine a desired dose of drug to permeate or be dispensed or absorbed into the target tissue, and to measure, monitor, calculate or otherwise estimate attainment or progress towards that pharmacokinetic goal during or at the end of a treatment session. To predetermine the desired dose, it may be useful to estimate the volume of tissue targeted for saturation with the drug molecules from drug solution 30. Target tissue volume may be estimated based on the surface area of the tissue within the treatment chamber in a given patient. To predetermine the desired dose, it may also be useful to know or estimate the rate of transfer of the drug through the wall of the natural lumen and into the target tissue area.

One parameter that may be used to calculate the exposed tissue surface area may be the liquid capacity of the treatment chamber as measured by the volume of liquid pumped into the fluid circuit during the air purging step. For example, drug solution 30 or sterile saline may be admitted by a graduated syringe to the ingress port via one of connecting ports 15 or 16 shown in FIG. 6, and the volume of admitted drug solution 30 is measured when the liquid begins to appear at the other of connecting ports 15 or 16 in fluid communication with the purge port. Other parameters that may be used to calculate the exposed tissue surface area may be a known distance between the pair of expandable members, a diameter of at least one of the expandable members, a distance from the natural orifice of the natural lumen to the two or more expandable members, an analysis of current and/or previous medical images of the natural lumen extending through the target tissue area of the internal body organ of the patient, and a statistical analysis of historical data regarding physical dimensions of similar natural lumens extending through similar target tissue areas for a known population of patients. The diameter of at least one of the expandable members may be measured from a medical image or the expandable member may be an inflatable elastic balloon and a diameter of the balloon is determined based at least in part on a volume of a fluid or air used to inflate the balloon into sealing contact with the inner wall of the natural lumen.

A treatment session may be terminated when the desired drug dose has been delivered to the target tissue. The amount of drug delivered via the treatment chamber may be estimated using parameters including the volume of the closed-loop fluid circuit, the volume of the target tissue, and the change in concentration of the drug in recirculating drug solution 30. Thus, the amount of drug calculated as missing from the volume of liquid in the closed-loop fluid circuit is presumed to have permeated into the target tissue.

An alternative method of estimating the amount of drug delivered during a treatment session may be based on elapsed time and parameters such as a known permeability rate for a given concentration of drug in a given tissue type. Such parameters may be drawn from data regarding a general population rather than requiring data from the current patient. In this method, the size of the surface area of target tissue may or may not be useful to determine whether the desired drug dose has been delivered to the target tissue.

Another method in accordance with an embodiment of the present technology may continue recirculating liquid drug solution 30 through the closed-loop fluid circuit beyond the point of saturating target tissue with a selected anti-cancer drug. The drug may permeate the target tissue, enter and activate the lymphatic system 22 or interstitial space, all of which may act as a conduit or reservoir for the drug to continue eluting drug into cancerous tissue after the session has been terminated and the catheter is removed from the patient.

Another method in accordance with an embodiment of the present technology is to fill the treatment chamber with drug solution 30 of a known, e.g. calculated drug concentration for a selected period of time without circulation or recirculation. That is, drug solution 30 carries a measured amount of the drug and remains stationary in the treatment chamber for a duration that is expected to achieve the desired drug dosing.

When the desired drug dosing has been achieved and the treatment session is terminated, the treatment chamber may be evacuated by pumping a flushing fluid therethrough, in similar fashion to the air purging step described above. A non-toxic flushing fluid such as air, saline, or other gases or liquids may be used to clear drug solution 30 from the treatment chamber, leaving the flushing fluid therein. Clearing the anti-cancer drug from the treatment chamber may prevent target tissue from being exposed to the drug for a longer time than desired, and/or may prevent non-target tissue from being exposed to the drug when the treatment chamber is broken down by returning expandable members 11, 12 to the collapsed delivery configuration to permit removal of catheter 10 from the patient.

Figure 2:
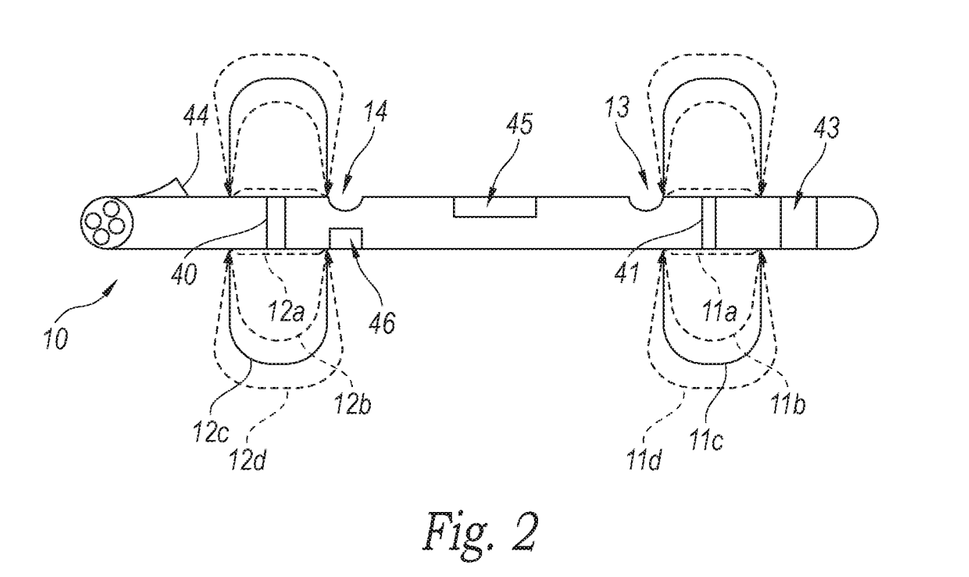
FIG. 2 shows a distal portion of a catheter in accordance with another embodiment of the disclosure.
Figure 3:
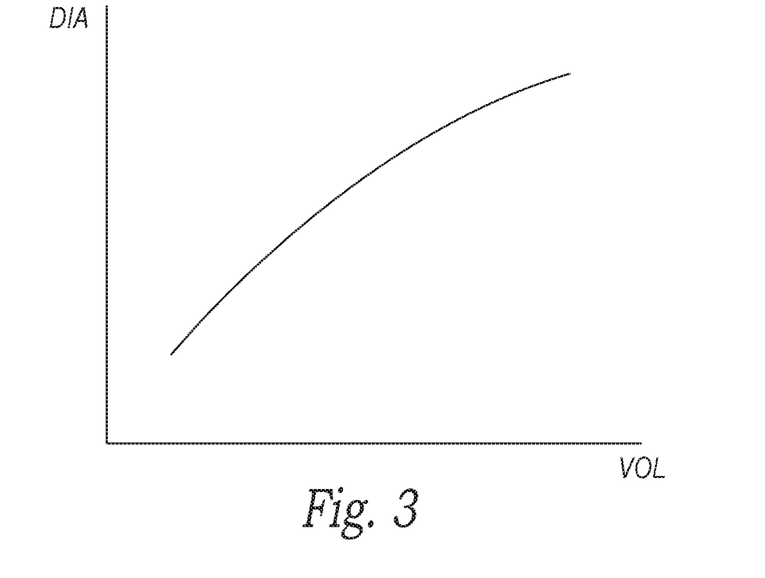
FIG. 3 is a graph of an exemplary known relationship of diameter to inflation volume for a sealing balloon in accordance with the disclosure.

FIG. 2. illustrates a distal region of another catheter 10 configured in accordance with an embodiment of the present technology. Expandable members 11, 12 are shown with variable diameters including fully collapsed respective configurations 11a, 12a, and increasingly larger configurations 11b, 12b; 11c, 12c; and 11d, 12d. The variability in diameter of expandable members 11, 12 allows each member to be selectively expanded into sealing engagement with a natural lumen such as the colon illustrated in FIG. 1. Expandable members 11, 12 may be inflatable elastic balloons, wherein each balloon has a diameter that corresponds in a known relationship to either a gas pressure or a liquid volume, as illustrated in FIG. 3. The selected balloon may be characterized as compliant, non-compliant, elastic or inelastic, depending on its diameter-to-volume or diameter-to-pressure properties. In an example, a catheter having an inelastic balloon may be selected in cases where the known inflated diameter of the balloon can be expected to create an effective treatment chamber seal at the intended anatomic location. In the case of expandable members 11, 12 having two balloons, the balloons may be inflated together or separately, to the same or different diameters, and via common or separate inflation lumens 17, 18 shown in FIG. 6, as would be known to those of skill in the field of balloon catheters. Ports 13, 14 are illustrated as being positioned as close to expandable members 11, 12 as possible. The shape of the expanded members 11, 12 and the very adjacent location of the ports thereto can be selected to optimize purging of air from the treatment chamber. E.g. a balloon may be mounted to catheter 10 with an inverted neck (not shown) to permit locating a port closer to the expandable body of the balloon. Additionally, or alternatively, the expandable member may have a concave or invaginated surface facing towards the treatment chamber to enhance air purging by directing air away from the lumen wall and towards the egress port in the catheter shaft.

The embodiment of catheter 10 shown in FIG. 2 has the following optional features. Fiducial markers 40, 41 may be associated with expandable members 11, 12. In order to assist in locating the treatment chamber with respect to a target area, markers 40, 41 may be visible under medical imaging, e.g. radiopaque markers for visualization under fluoroscopy or sensors (like electromagnetic coils) for use in navigation systems. Orientation sensor 43 may be located proximate the distal region of catheter 10 to inform the operator of the angle of catheter 10 with respect to gravity. The axis of the distal region of catheter 10 is expected to be generally coaxial with the treatment chamber due to the centering effect of expandable members 11, 12. Orientation sensor 43 may be an accelerometer adapted to communicate with an electronic console exterior to the patient. Camera 44 may be located proximate the distal region of catheter 10 to assist in locating the treatment chamber with respect to a target area. The camera may use optical coherence tomography (OCT) or other small medical camera technologies. Pressure sensor 45 may be located between expandable members 11, 12 to provide data regarding fluid pressure within the treatment chamber. The pressure sensor may utilize the piezoelectric effect or other technologies, with the pressure data being useful to monitor and/or maintain safe and effective pressure within the treatment chamber and to potentially detect leakage from the chamber. One or more electrodes 46 may be located between the expandable members and positioned as close as possible thereto. Electrode 46 may be used to monitor electrical impedance, which may be useful to detect when the treatment chamber has filled with liquid or monitor changes in drug concentration.

Figure 5:
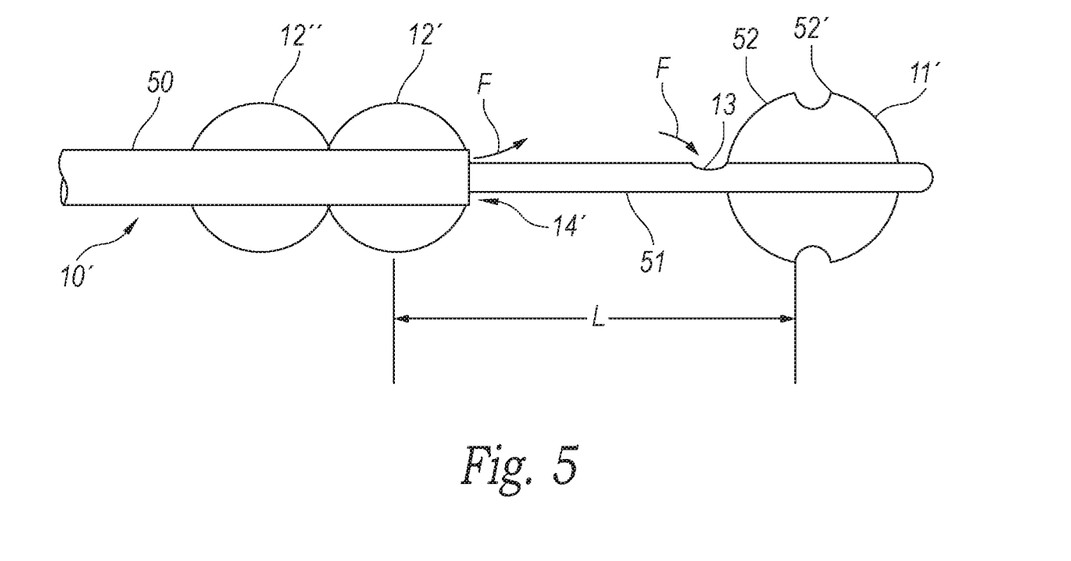
FIG. 5 shows a distal portion of a catheter in accordance with another embodiment of the disclosure.

The embodiment of catheter 10' shown in FIG. 5 has the following optional features. Catheter 10' comprises a first catheter shaft 50 having an expandable member 12' mounted at the distal end thereof. A second catheter shaft 51 is slidably disposed within a lumen through shaft 50 and extends distally therefrom. Expandable member 11' is mounted about a distal region of shaft 51. The operator may adjust how much of shaft 51 extends from shaft 50 to selectively define the length L of the treatment chamber formable between expandable members 11', 12'. Port 14' may be an annular clearance space at the terminus of the lumen in shaft 50 that slidably receives shaft 51. Ports 13 and 14' may function as shown in previous embodiments, including their reversibility, as described above.

Catheter 10' also comprises a second expandable member 12" mounted adjacent expandable member 12' to provide additional sealing capability against a luminal wall beyond that provided by member 12' alone. This additional, adjacent balloon could serve as a redundant safety feature should sealing of one of the balloons fail. Additional sensors (electrodes, cameras, pressure monitors, etc.) may be placed between these balloons to monitor for fluids indicating a failed seal. Expandable member 11' comprises multiple lobes 52, 52' that may also provide additional sealing capability against a luminal wall. A plurality of expandable members, balloons, or lobes may thus be provided to form one or both ends of a treatment chamber in accordance with embodiments of the present technology.

FIG. 6 illustrates a drug delivery system 60 configured in accordance with an embodiment of the present technology. System 60 includes catheters 10 or 10' operably coupled to a console 62. Alternatively, system 60 may include other catheters in accordance with the present technology, such as catheters 710, 810 described below. Catheter 10 includes selected features of the catheter embodiments described above, and further includes a flexible elongate shaft 63, a proximal portion 64, and a distal portion 65. Fluid connectors 15, 16 are in fluid communication with ports 13, 14 at distal region 65 and may be attached directly or via extension tubes (shown in broken lines) to console 62. Inflation lumens 17, 18 are in fluid communication with expandable members at distal region 65 and may be in communication with separate inflation devices (not shown), or may be connected to console 62 in an embodiment where inflation devices are incorporated therein.

Console 62 may incorporate or be operably coupled to several components adapted to serve different functions as follows. A reservoir 66 may contain drug solution 30; a pump 67 may recirculate the drug solution 30 via catheter fluid connectors 15, 16; and an osmometer 68 may monitor the concentration of the drug in recirculating drug solution 30. A pressure sensor 69 may electronically communicate with pressure sensor 45 shown in FIG. 2, or may directly measure pressure in recirculating drug solution 30 within console 62. Control unit 70 may operate pump 67 based at least in part on one or more inputs selected from elapsed time, instantaneous pressure in the closed-loop recirculating fluid circuit, amount of the drug solution 30 added to the fluid circuit, instantaneous drug concentration of the drug solution 30 occupying the closed-loop recirculating fluid circuit, and manual data entered by an operator, e.g. by a keypad 71 on console 62. The pressure in the closed-loop recirculating fluid circuit may be established, maintained, and changed by pump 67. For example, pump 67 may provide a partial vacuum, a.k.a. negative pressure to the egress lumen and egress port to help evacuate the treatment chamber in preparation for administering drug solution 30 at the beginning of a treatment session or for clearing the treatment chamber of drug solution 30 at the end of a treatment session. Pump 67 may also maintain pressure of drug solution 30 in the treatment chamber at a selected elevated level, e.g. above atmospheric pressure or above patient blood pressure, to enhance or facilitate uptake of the drug into the target tissue while limiting the selected pressure to avoid injury to tissue or leakage of drug solution 30 past the seal(s) form by the expandable member(s) at the end(s) of the treatment chamber. Alternatively, the pressure of drug solution 30 in the treatment chamber may be maintained at close to atmospheric pressure by pump 67, or by a gravity-feed directly from reservoir 66 without the use of a pump. Furthermore, instead of using a powered pump 67, liquid drug solution 30 may be circulated through the closed fluid circuit by pushing a fixed volume of liquid drug solution 30 between first and second external reservoirs, e.g. first and second syringes connected to ports 15, 16, as mentioned above.

Figure 7:
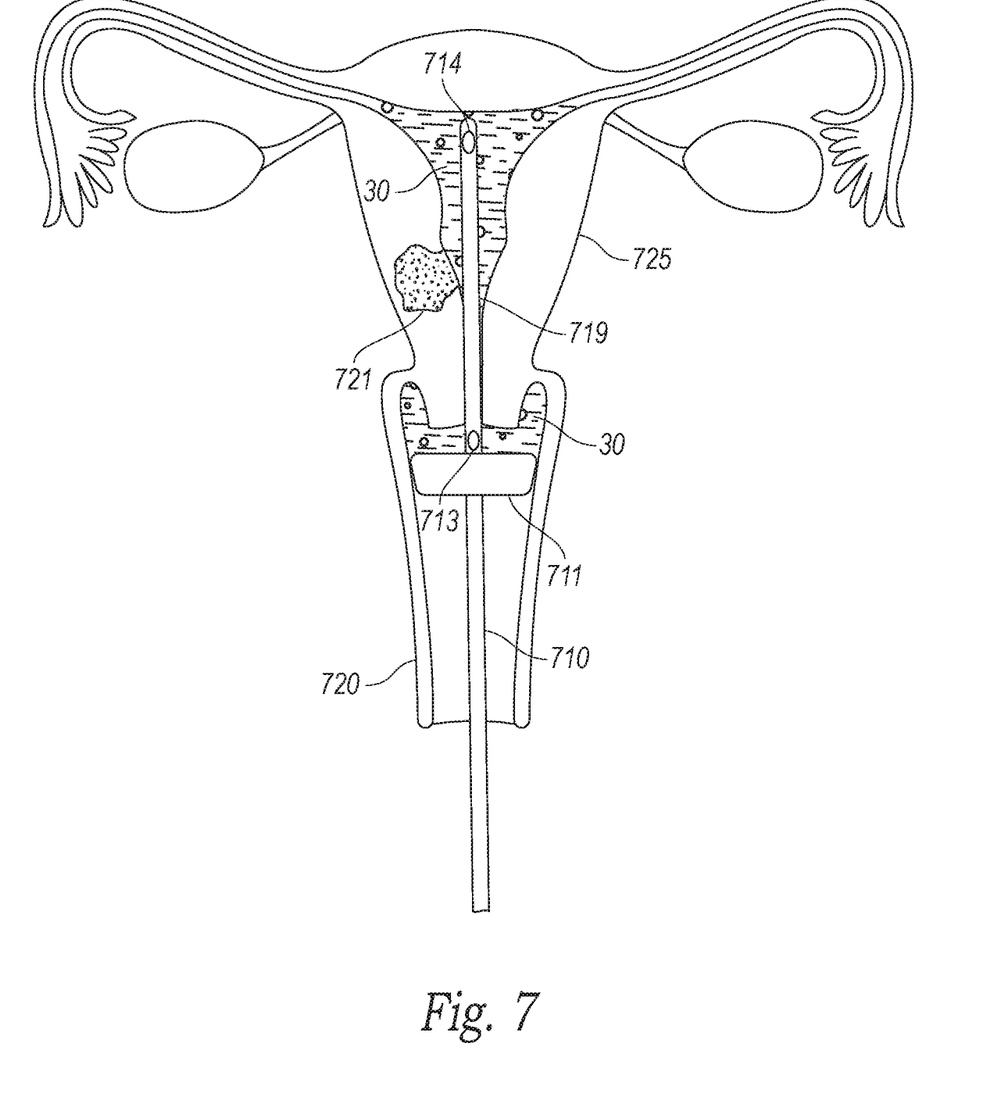
FIG. 7 illustrates a chemotherapeutic treatment of a portion of a female genital tract using a catheter in accordance with another embodiment of the disclosure.

FIG. 7 illustrates a catheter 710 in accordance with another embodiment of the present technology. Catheter 710 is shown in a deployed configuration within a target region of a female genital tract including a portion of a vagina 720 and uterus 725. An expandable member 711 is mounted about a distal region 719 of catheter 710, and is adapted to be expanded into sealing contact with the inner wall of uterus 725, or, as illustrated, with the inner wall of vagina 720. A treatment chamber is defined as the portion of the natural lumen or genital tract distal of expandable member 711. In the illustrated embodiment, the treatment chamber includes a uterine cancer 721. Catheter distal region 719 extends distally of expandable member 711 by a length that may be fixed and selectively pre-designed or that may be variable and selectively adjusted by the operator, similar to length L in catheter 10' described above and shown in FIG. 5. Port 713 is disposed distally adjacent expandable member 711 and port 714 is disposed at or adjacent the distal end of distal region 719. In the illustrated embodiment, expandable member 711 extends to the fundus of the uterus and thereby positions port 714 at or near the distalmost extent of the desired treatment chamber. Ports 713, 714 fluidly communicate the treatment chamber with respective lumens (not shown) that extend proximally through the catheter to terminate at respective connectors located at the proximal end thereof, comparable to connectors 15, 16 shown in FIG. 6. This embodiment demonstrates a treatment chamber that is defined by the force of gravity and the location of the egress port 714. The proximal end of the treatment chamber may or may not be defined by an expandable member, as described below.

Once catheter 710 has been deployed as shown in FIG. 7, the operator may assess the orientation of the treatment chamber with respect to gravity G, and may reposition the patient, if necessary, to orient the treatment chamber as close to vertical as possible, as described above with respect to catheter 10 in FIG. 1. In the treatment illustrated in FIG. 7, port 714 may be defined as the egress port and port 713 may be defined as the ingress port. After the treatment chamber is oriented with respect to gravity, a liquid drug solution 30 is admitted or forced into the chamber via the ingress port, i.e. port 713 in FIG. 7. As liquid drug solution 30 fills the treatment chamber from bottom to top, air is purged from the chamber via the egress port, i.e. port 714 until the liquid drug solution reaches port 714. In this way, the treatment chamber is filled with liquid drug solution 30, leaving only a small air bubble or preferably no bubble at all. The avoidance of air bubbles or air pockets may ensure that all of the inner wall of female genital tract in the treatment chamber is bathed in liquid drug solution 30. Liquid drug solution 30 may be circulated or recirculated through the treatment chamber between ingress port 713 and egress port 714 as described above with respect to the embodiment shown in FIG. 1. Alternatively, the treatment chamber may be filled with drug solution 30 of a known, e.g. calculated drug concentration for a selected period of time without circulation or recirculation. The treatment chamber may also be evacuated, as described above, by forcing a flushing fluid therethrough using ports 713, 714.

The extent of the treatment chamber formed in the hollow anatomical space may be controlled by limiting the volume or pressure of liquid drug solution 30 admitted or forced into the treatment chamber via catheter 710. In the example illustrated in FIG. 7, liquid drug solution 30 has not been forced into the fallopian tubes from the uterus, although extending the treatment chamber into these spaces may desirable for treatment of cancer in the fallopian tubes or the ovaries. Since the ostia of the fallopian tubes are proximate to but not in direct connection with the respective ovaries, any liquid drug solution 30 that is forced all the way through one or both fallopian tubes may enter and begin to fill the peritoneal cavity and may result in either intentional or unintentional intraperitoneal chemotherapy. Catheter 710 may be selectively designed or placed such that expandable member 711 creates the proximal end of a treatment chamber in the uterus, or in the vagina, as illustrated. Thus, cancer in various locations throughout the female genital tract may be treated by exposing target tissue to liquid drug solution 30. Alternatively, catheters 10, 10' may be adapted to create a treatment chamber bounded at its ends by two or more expandable members selectively spaced apart and positioned along the female genital tract from the vaginal vestibule, through the cervix, to the fundus of the uterus. In another alternative in accordance with an embodiment of the present technology (not shown), a catheter or catheters may be adapted to operate solely or in combination to create a female genital tract treatment chamber wherein at least distal portions of one or both fallopian tubes are excluded therefrom by expandable member(s) deployed within the respective fallopian tube(s).

Catheter 710 features a single expandable member and two spaced-apart ports disposed distally thereof such that a treatment chamber for use in chemotherapy can be created distally of the expandable member. Although not illustrated, it will be apparent to persons skilled in the relevant art that the scope of the invention includes catheters, systems and methods wherein two ports are disposed proximally of a single expandable member such that a treatment chamber for use in chemotherapy can be created proximally of the expandable member.

Furthermore, it will be apparent to persons skilled in the relevant art that the scope of the invention includes catheters, systems and methods wherein a catheter having two spaced-apart ports but without any expandable member can seal within the cervix and thereby form a treatment chamber distally thereof, including the uterus. Such a balloonless catheter may be a modification of any catheter disclosed herein, for example catheter 10' of FIG. 5 wherein shaft 50 may be modified to fit sealably within the cervix, especially the cervix of a nulliparous female patient having a very small cervical opening.

Figure 8:
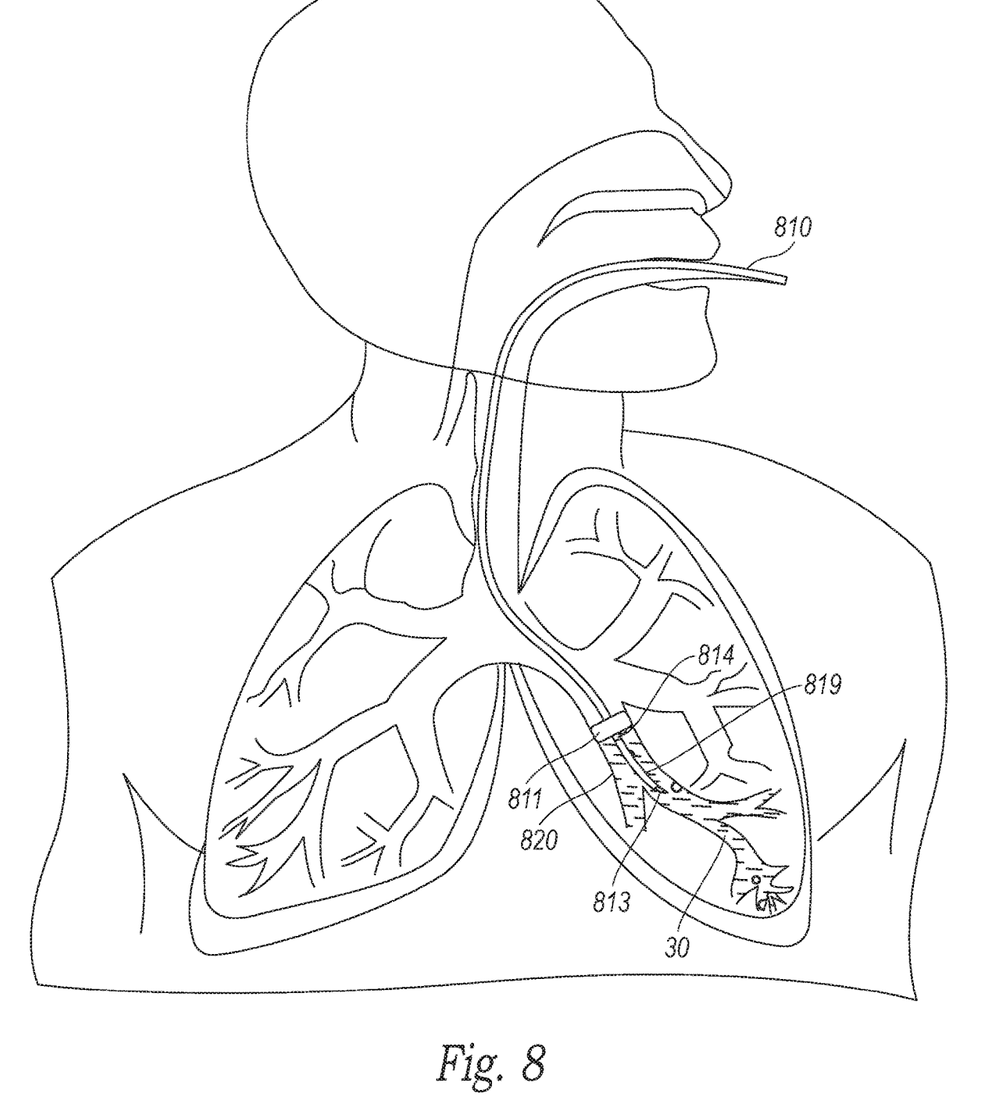
FIG. 8 illustrates a chemotherapeutic treatment of a portion of a respiratory tract using a catheter in accordance with another embodiment of the disclosure.

FIG. 8 illustrates a catheter 810 configured in accordance with another embodiment of the present technology. Catheter 810 is shown in a deployed configuration within a target region of a respiratory tract. Catheter distal region 819 extends distally of expandable member 811 by a length that may be fixed and selectively pre-designed or that may be variable and selectively adjusted by the operator, similar to length L in catheter 10' described above and shown in FIG. 5. Expandable member 811 is mounted about distal region 819 of catheter 810, and is adapted to be expanded into sealing contact with the inner wall of a segmental bronchus 820, as shown. Port 813 is disposed distal and very adjacent expandable member 811 and port 814 is disposed at or adjacent the distal end of distal region 819. A treatment chamber is defined as the portion of the natural lumen or respiratory tract distal of expandable member 811. Catheter 810 may be adapted, if necessary for creating treatment chambers in different parts of the bronchi of the respiratory tract. The structure and use of catheter 810 is comparable to that of catheter 710 described above and shown in FIG. 7. The patient may be repositioned as described above to optimize orientation of the treatment chamber for purging air therefrom, and ports 813, 814 may be used in similar fashion to ports 13, 14, 713, 714 as described above to purge air and to circulate or recirculate drug solution 30. The treatment chamber may also have air evacuated therefrom before treatment, and/or liquid drug solution cleared out by forcing a flushing fluid therethrough using ports 813, 814.

The following chemotherapeutic drugs are considered to be usable with the technology of the disclosure, but are merely given as examples, and not by way of limitation: vinblastine (VELBE), vinorelbine (NAVELBINE), irinotecan (CAMPTOSAR), paclitaxel (TAXOL), docetaxel (TAXOTERE), epirubicin (ELLENCE), doxorubicin (ADRIAMYCIN), capecitabine (XELODA), etoposide (ETOPOPHOS), topotecan (HYCAMTIN), pemetrexed (ALIMTA), carboplatin (PARAPLATIN), fluorouracil (ADRUCIL), gemcitabine (GEMZAR), oxaliplatin (ELOXATIN), cisplatin (PLATINOL), trastuzumab (HERCEPTIN), ramucirumab (CYRAMZA), and bevacizumab (AVASTIN).

Further examples include the following:

Example 1 includes a catheter for delivery of a drug to a target tissue area of an internal body organ of a patient, the catheter having an elongate flexible shaft and two longitudinally spaced-apart expandable members disposed about a catheter shaft distal region, the expandable members being transformable between a collapsed delivery configuration and an expanded configuration for sealing against a natural lumen extending through the target tissue area to form a closed treatment chamber defined between the two expandable members and the wall of the natural lumen, the catheter further having first and second drug-delivery lumens extending from a catheter proximal end to respective first and second ports disposed between the expandable members.

Example 2 includes the catheter of example 1, further including an orientation sensor mounted at the catheter shaft distal region.

Example 3 includes the catheter of any of examples 1 or 2, wherein the two expandable members comprise respectively two compliant balloons wherein each balloon is inflatable to varying diameters, the catheter further having one or more inflation lumens extending from the catheter proximal end to the expandable members for inflating each of the compliant balloons either together or independently.

Example 4 includes the catheter of any of examples 1-3, further including a navigation camera disposed adjacent the distal region.

Example 5 includes the catheter of any of examples 1-4, further including two fiducial markers for referencing the respective locations of the two expandable members when the catheter is viewed using a medical imaging system or a navigation system.

Example 6 includes the catheter of any of examples 1-5, wherein the two longitudinally spaced-apart expandable members are configured for forming a closed treatment chamber within a lumen of a gastrointestinal tract, a female genital tract, a urinary tract, or a respiratory tract.

Example 7 includes a catheter for local delivery of a drug to a target tissue area of an internal body organ of a patient, the catheter including: an elongate flexible shaft; first and second longitudinally spaced-apart expandable members disposed about a distal region of the flexible shaft, the expandable members each being transformable between a collapsed delivery configuration and an expanded configuration for sealing against the wall of a natural lumen extending through the target tissue area to form a closed treatment chamber defined between the first and second expandable members and the wall of the natural lumen; a liquid ingress lumen extending from a shaft proximal end to a liquid ingress port located between the expandable members; and a liquid egress lumen extending from a shaft proximal end to a liquid egress port located between the expandable members; wherein the functions of the ingress and egress ports are reversible such that either port can be a high point of the formed treatment chamber with respect to gravity.

Example 8 includes the catheter of example 7, further including an orientation sensor mounted at the shaft distal region and operable to indicate to an operator the orientation of the shaft distal region with respect to gravity.

Example 9 includes the catheter of example 8, wherein the orientation sensor is an accelerometer adapted to communicate with an electronic console exterior to the patient.

Example 10 includes the catheter of any of examples 7-9, wherein the liquid ingress port is located very adjacent the first expandable member and the liquid egress port is located very adjacent the second expandable member.

Example 11 includes the catheter of any of examples 7-10, wherein both the first and second expandable members are compliant balloons inflatable to varying diameters, the shaft further having one or more inflation lumens configured for inflating the compliant balloons either simultaneously or independently.

Example 12 includes the catheter of any of examples 7-11, further including a navigation camera disposed adjacent the distal region.

Example 13 includes the catheter of any of examples 7-12, further including one or more fiducial markers for referencing the respective locations of the first and second expandable members when the catheter is viewed using a medical imaging system or a navigation system.

Example 14 includes the catheter of any of examples 7-13, wherein the first and second longitudinally spaced-apart expandable members are configured for forming a closed treatment chamber within a lumen of a gastrointestinal tract, a female genital tract, a urinary tract or a respiratory tract.

Example 15 includes the catheter of any of examples 7-14, further including one or more electrodes disposed between the first and second longitudinally spaced-apart expandable members.

Example 16 includes the catheter of example 15, wherein the electrodes are configured and located to provide an impedance indication when liquid reaches the high point of the formed treatment chamber with respect to gravity.

Example 17 includes the catheter of example 15, wherein the electrodes are configured and located to provide an impedance indication of a concentration of the drug in the drug solution.

Example 18 includes a method for local delivery of a drug to a target tissue area of an internal body organ of a patient, the method including: inserting a distal region of an elongate flexible catheter shaft through a natural orifice into a natural lumen extending through the target tissue area; transforming two expandable members on the shaft distal region from a collapsed delivery configuration to an expanded configuration in sealing engagement with a wall of the natural lumen to thereby form a closed treatment chamber defined between the two expandable members and the wall of the natural lumen; and circulating a liquid drug solution for the duration of a treatment session through a closed fluid circuit that comprises the treatment chamber and two drug-delivery lumens that both extend through the catheter shaft from two respective connecting ports exterior to the patient to two respective chamber ports disposed in the shaft distal region between the expandable members.

Example 19 includes the method of example 18, and further includes: purging air from the treatment chamber before circulating a liquid drug solution, the purging including: determining the orientation of the shaft distal region with respect to gravity; repositioning the patient, if necessary, such that a one of the chamber ports is located at a high point of the treatment chamber with respect to gravity and defining the port so located as a purge port; defining the other chamber port located below the purge port in the treatment chamber as a fill port; and filling the treatment chamber with the liquid drug solution through the fill port while permitting air to exit through the purge port.

Example 20 includes the method of example 19, further including applying negative pressure to the drug-delivery lumen extending from the purge port to enhance purging of air from the treatment chamber.

Example 21 includes the method of example 19, wherein the purge port is located very adjacent to one of the expandable members.

Example 22 includes the method of any of examples 18-21, further including: terminating the treatment session; and evacuating the treatment chamber of liquid drug solution after terminating the treatment session.

Example 23 includes the method of any of examples 18-22, further including: measuring a change in a drug concentration in the circulating drug solution over at least a portion of the treatment session; measuring an elapsed treatment session time; and calculating an amount of the drug that is dispensed from the treatment chamber based at least in part on the measured change in drug concentration, the measured elapsed treatment session time and a known permeability rate for a given concentration of the drug in a given tissue type.

Example 24 includes the method of example 23, further including terminating the treatment session if the calculated amount of the drug dispensed from the treatment chamber equals or exceeds a predetermined maximum threshold amount.

Example 25 includes the method of example 23, further including terminating the treatment session if the calculated amount of the drug dispensed from the treatment chamber is within a predetermined therapeutic window.

Example 26 includes the method of example 18, further including: measuring a drug concentration in the circulating drug solution during the treatment session; and terminating the treatment session if the measured drug concentration is equal to or less than a predetermined minimum threshold amount.

Example 27 includes the method of example 25, wherein maximum and minimum drug dosage values define the therapeutic window and the drug dosage values are calculated based at least in part on a desired amount of the drug to be absorbed and an estimated surface area of the wall of the natural lumen in the treatment chamber.

Example 28 includes the method of example 27, wherein the surface area of the luminal wall in the treatment chamber is estimated based at least in part on one or more of the following parameters: a known distance between the two expandable members; a diameter of at least one of the two expandable members; a distance from the natural orifice of the natural lumen to one of the two expandable members; an analysis of current and/or previous medical images of the natural lumen extending through the target tissue area of the internal body organ of the patient; a liquid capacity of the treatment chamber measured when filling the treatment chamber before circulating a liquid drug solution; and a statistical analysis of historical data regarding physical dimensions of similar natural lumens extending through similar target tissue areas for a known population of patients.

Example 29 includes the method of example 28, wherein the diameter of at least one of the expandable members is measured from a medical image or the at least one of the expandable members is an inflatable elastic balloon and a diameter of the balloon is determined based at least in part on a volume used to inflate the balloon.

Example 30 includes the method of examples 28 or 29, further including: estimating the volume of the target tissue area based at least in part on one or more of the following parameters: a known distance between the two expandable members; a diameter of at least one of the two expandable members; a distance from the orifice of the natural lumen to one of the two expandable members; an analysis of current and/or previous medical images of the natural lumen extending through the target tissue area of the internal body organ of the patient; a liquid capacity of the treatment chamber measured when filling the treatment chamber before recirculating a liquid drug solution; and a statistical analysis of historical data regarding physical dimensions of similar natural lumens extending through similar target tissue areas for a known population of patients; and calculating a desired amount of the circulating liquid drug to be delivered based at least in part on one or more inputs selected from the estimated surface area of the treatment chamber, the estimated volume of the target tissue area, and a known rate of transfer of the drug through the wall of the natural lumen and into the target tissue area.

Example 31 includes the method of example 23, wherein measuring a change in the drug concentration in the circulating drug solution is performed using an osmometer.

Example 32 includes the method of any of examples 18-31, wherein circulating the liquid drug solution achieves homogeneous concentration of the drug in the drug solution within in the treatment chamber.

Example 33 includes the method of any of examples 18-32, wherein transforming two expandable members further comprises adjusting a longitudinal distance between the expandable members such that the length of the closed treatment chamber corresponds with a length of the target tissue area.

Example 34 includes the method of any of examples 18-33, wherein circulating the liquid drug solution further comprises continuing to circulate the liquid drug solution until the drug has saturated the target tissue area and passed therethrough into the surrounding interstitial space or the proximate lymphatic system of the patient, all of which may act as a conduit or reservoir for the drug.

Example 35 includes a method for local delivery of a drug to a target tissue area of an internal body organ of a patient, the method including: inserting a distal region of an elongate flexible catheter shaft through a natural orifice into a natural lumen extending through the target tissue area; transforming two expandable members on the shaft distal region from a collapsed delivery configuration to an expanded configuration in sealing engagement with a wall of the natural lumen to thereby form a closed treatment chamber defined between the two expandable members and the wall of the natural lumen; and recirculating a liquid drug solution for the duration of a treatment session through a closed-loop fluid circuit that comprises the treatment chamber and two drug-delivery lumens that both extend through the catheter shaft from two respective connecting ports exterior to the patient to two respective chamber ports disposed in the shaft distal region between the expandable members.

Example 36 includes the method of example 35, further including: purging air from the treatment chamber before recirculating a liquid drug solution, the purging including: determining the orientation of the shaft distal region with respect to gravity; repositioning the patient, if necessary, such that a one of the chamber ports is located at a high point of the treatment chamber with respect to gravity and defining the port so located as a purge port; defining the other chamber port located below the purge port in the treatment chamber as a fill port; and filling the treatment chamber with the liquid drug solution through the fill port while permitting air to exit through the purge port.

Example 37 includes the method of example 36, further including applying negative pressure to the drug-delivery lumen extending from the purge port to enhance purging of air from the treatment chamber.

Example 38 includes the method of example 36, wherein the purge port is located very adjacent to one of the expandable members.

Example 39 includes the method of any of examples 35-38, further including: terminating the treatment session; and evacuating the treatment chamber of liquid drug solution after terminating the treatment session.

Example 40 includes the method of any of examples 35-39, further including: measuring a change in a drug concentration in the recirculating drug solution over at least a portion of the treatment session; measuring an elapsed treatment session time; and calculating an amount of the drug that is dispensed from the treatment chamber based at least in part on the measured change in drug concentration, the measured elapsed treatment session time and a known permeability rate for a given concentration of the drug in a given tissue type.

Example 41 includes the method of example 40, further including terminating the treatment session if the calculated amount of the drug dispensed from the treatment chamber equals or exceeds a predetermined maximum threshold amount.

Example 42 includes the method of example 40, further including terminating the treatment session if the calculated amount of the drug dispensed from the treatment chamber is within a predetermined therapeutic window.

Example 43 includes the method of example 35, further including: measuring a drug concentration in the recirculating drug solution during the treatment session; and terminating the treatment session if the measured drug concentration is equal to or less than a predetermined minimum threshold amount.

Example 44 includes the method of example 42, wherein maximum and minimum drug dosage values define the therapeutic window and the drug dosage values are calculated based at least in part on a desired amount of the drug to be absorbed and an estimated surface area of the wall of the natural lumen in the treatment chamber.

Example 45 includes the method of example 44, wherein the surface area of the luminal wall in the treatment chamber is estimated based at least in part on one or more of the following parameters: a known distance between the two expandable members; a diameter of at least one of the two expandable members; a distance from the orifice of the natural lumen to one of the two expandable members; an analysis of current and/or previous medical images of the natural lumen extending through the target tissue area of the internal body organ of the patient; a liquid capacity of the treatment chamber measured when filling the treatment chamber before recirculating a liquid drug solution; and a statistical analysis of historical data regarding physical dimensions of similar natural lumens extending through similar target tissue areas for a known population of patients.

Example 46 includes the method of example 45, wherein the diameter of at least one of the expandable members is measured from a medical image or the at least one of the expandable members is an inflatable elastic balloon and a diameter of the balloon is determined based at least in part on a volume used to inflate the balloon.

Example 47 includes the method of example 45, further including: estimating the volume of the target tissue area based at least in part on one or more of the following parameters: a known distance between the two expandable members; a diameter of at least one of the two expandable members; a distance from the orifice of the natural lumen to one of the two expandable members; an analysis of current and/or previous medical images of the natural lumen extending through the target tissue area of the internal body organ of the patient; a liquid capacity of the treatment chamber measured when filling the treatment chamber before recirculating a liquid drug solution; and a statistical analysis of historical data regarding physical dimensions of similar natural lumens extending through similar target tissue areas for a known population of patients; and calculating a desired amount of the circulating liquid drug to be delivered based at least in part on one or more inputs selected from the estimated surface area of the treatment chamber, the estimated volume of the target tissue area, and a known rate of transfer of the drug through the wall of the natural lumen and into the target tissue area.

Example 48 includes the method of example 40, wherein measuring a change in the drug concentration in the recirculating drug solution is performed using an osmometer.

Example 49 includes the method of example 40, wherein the steps of recirculating a liquid drug solution, measuring a change in a drug concentration in the recirculating drug solution, and calculating the amount of the drug absorbed from the treatment chamber are performed by a system including a pump, an osmometer, and a control unit configured to operate the pump based at least in part on one or more inputs selected from elapsed time, instantaneous pressure in the closed-loop fluid circuit, amount of the drug solution added to the fluid circuit, instantaneous drug concentration of the drug solution occupying the closed-loop fluid circuit, and manual data entered by an operator.

Example 50 includes the method of example 35, further including: monitoring a fluid pressure in the closed-loop fluid circuit.

Example 51 includes the method of example 50, further including maintaining the fluid pressure in the closed-loop fluid circuit within a predetermined pressure range.

Example 52 includes the method of example 51, wherein the predetermined pressure range includes a positive pressure sufficient to enhance uptake of drug into the target tissue area.

Example 53 includes the method of example 51, wherein if the monitored fluid pressure exceeds the predetermined pressure range, then a pumping pressure is reduced by a recirculating pump in the closed-loop fluid circuit.

Example 54 includes the method of example 51, wherein if the monitored fluid pressure is below the predetermined pressure range, then a pumping pressure is increased by a recirculating pump in the closed-loop fluid circuit and/or additional drug solution or solvent is added to the closed-loop fluid circuit.

Example 55 includes the method of example 50, further including terminating the recirculating of a drug solution if a leak in the treatment chamber is indicated by one or more of the following conditions: the fluid pressure in the closed-loop fluid circuit drops below a predetermined minimum pressure; a calculated rate of pressure change in the closed-loop fluid exceeds a predetermined rate of change, and a medical image of the patient shows that one or both of the expandable members is not sufficiently sealing against the wall of the natural lumen.

Example 56 includes the method of example 50, wherein the fluid pressure in the closed-loop fluid circuit is monitored by a pressure sensor mounted on the catheter in the treatment chamber or a pressure sensor located in an electronic console exterior to the patient and in fluid communication with the closed-loop fluid circuit.

Example 57 includes the method of example 35, further including flushing the drug solution from the closed-loop fluid circuit at the end of the treatment session.

Example 58 includes the method of example 35, wherein recirculating the liquid drug solution further comprises pumping the liquid drug solution from a pump through one of the two drug-delivery lumens to the treatment chamber while permitting the liquid drug solution to return from the treatment chamber to the pump via the other of the two drug-delivery lumens.

Example 59 includes a method for local delivery of a liquid drug to a target tissue area surrounding a natural lumen extending through a female genital tract or a respiratory tract or a urinary tract or gastrointestinal tract of a patient, the method including: inserting a distal region of an elongate flexible catheter through a natural orifice into the natural lumen to a location proximate to the target tissue area; transforming an expandable member on the catheter from a collapsed delivery configuration to an expanded configuration that sealingly engages a wall of the natural lumen proximal to the target tissue area to thereby create a treatment chamber defined by the portion of the natural lumen distal of the expandable member; and circulating a liquid drug solution for the duration of a treatment session through a closed fluid circuit that comprises the treatment chamber and two drug-delivery lumens that both extend through the catheter shaft from two respective connecting ports exterior to the patient to two respective chamber ports disposed in the shaft region distal of the expandable member.

Example 60 includes the method of example 59, wherein transforming an expandable member further comprises adjusting a length of the catheter region distal of the expandable member to correspond with a length of the target tissue area.

Example 61 includes the method of any of examples 59-60, wherein circulating a liquid drug solution comprises delivering a known liquid drug concentration with a known tissue permeability of the drug concentration at a selected flow rate for a selected period of time.

Example 62 includes the method of any of examples 59-61, wherein circulating a liquid drug solution further comprises pushing a liquid other than the liquid drug through the catheter drug-delivery lumen to force the liquid drug from the catheter drug-delivery lumen into the treatment chamber.

Example 63 includes the method of any of examples 59-62, wherein the two respective chamber ports in the catheter region distal of the expandable member are longitudinally spaced-apart.

Example 64 includes the method of example 63, further including adjusting the distance that the chamber ports are spaced-apart to correspond with a length of the target tissue area.

Example 65 includes the method of any of examples 59-64, further including evacuating the treatment chamber before circulating a liquid drug solution.

Example 66 includes the method of any of examples 59-65 further including evacuating the treatment chamber of liquid drug solution after terminating the treatment session.

Example 67 includes the method of any of examples 59-66, further including: measuring a change in a drug concentration in the circulating drug solution over at least a portion of the treatment session; measuring an elapsed treatment session time; and calculating an amount of the drug that is dispensed from the treatment chamber based at least in part on the measured change in drug concentration, the measured elapsed treatment session time and a known permeability rate for a given concentration of the drug in a given tissue type.

Example 68 includes the method of any of examples 59-67, further including terminating the treatment session if the calculated amount of the drug dispensed from the treatment chamber equals or exceeds a predetermined maximum threshold amount.

Example 69 includes the method of any of examples 59-67, further including terminating the treatment session if the calculated amount of the drug dispensed from the treatment chamber is within a predetermined therapeutic window.

Example 70 includes the method of any of examples 59-67, further including: measuring a drug concentration in the circulating drug dose during the treatment session; and terminating the treatment session if the measured drug concentration is equal to or less than a predetermined minimum threshold amount.

Example 71 includes the method of example 69, wherein maximum and minimum drug dosage values define the therapeutic window and the drug dosage values are calculated before the drug solution is circulated based at least in part on a desired amount of the drug to be absorbed and an estimated surface area of the wall of the natural lumen in the treatment chamber.

Example 72 includes the method of example 71, wherein the surface area of the luminal wall in the treatment chamber is estimated based at least in part on one or more of the following parameters: a diameter of the expandable member; a distance from the orifice of the natural lumen to the expandable member; a distance from the expandable member to the chamber port located most distally therefrom; an analysis of current and/or previous medical images of the natural lumen extending through the target tissue area of the internal body organ of the patient; a liquid capacity of the treatment chamber measured when filling the treatment chamber before circulating a liquid drug solution; and a statistical analysis of historical data regarding physical dimensions of similar natural lumens extending through similar target tissue areas for a known population of patients.

Example 73 includes the method of example 72 wherein the diameter of the expandable member is measured from a medical image or the expandable member is an inflatable elastic balloon and a diameter of the balloon is determined based at least in part on a volume of a fluid used to inflate the balloon.

Example 74 includes the method of example 72, further including: estimating the volume of the target tissue area based at least in part on one or more of the following parameters: a diameter of the expandable member; a distance from the orifice of the natural lumen to the expandable member; a distance from the expandable member to the chamber port located most distally therefrom; an analysis of current and/or previous medical images of the natural lumen extending through the target tissue area of the internal body organ of the patient; a liquid capacity of the treatment chamber measured when filling the treatment chamber before circulating a liquid drug solution; and a statistical analysis of historical data regarding physical dimensions of similar natural lumens extending through similar target tissue areas for a known population of patients; and calculating a desired amount of the circulating liquid drug to be delivered based at least in part on one or more inputs selected from the estimated surface area of the treatment chamber, the estimated volume of the target tissue area, and a known rate of transfer of the drug through the wall of the natural lumen and into the target tissue area.

Example 75 includes the method of example 70, wherein measuring a change in the drug concentration in the circulating drug solution is performed using an osmometer.

Example 76 includes the method of example 59, wherein circulating a liquid drug solution through a closed fluid circuit further comprises recirculating the liquid drug solution through a closed-loop fluid circuit and the steps of recirculating a liquid drug solution, measuring a change in a drug concentration in the recirculating drug solution, and calculating the amount of the drug absorbed from the treatment chamber are performed by a system including a pump, an osmometer, and a control unit configured to operate the pump based at least in part on one or more inputs selected from elapsed time, instantaneous fluid pressure in the closed-loop fluid circuit, amount of the drug solution added to the fluid circuit, instantaneous drug concentration of the drug solution occupying the closed-loop fluid circuit, and manual data entered by an operator.

Example 77 includes the method of example 76, further including monitoring a fluid pressure in the closed-loop fluid circuit.

Example 78 includes the method of example 77, further including maintaining the fluid pressure in the closed-loop fluid circuit within a predetermined pressure range.

Example 79 includes the method of example 78, wherein the predetermined pressure range includes a positive pressure sufficient to enhance uptake of drug into the target tissue area.

Example 80 includes the method of example 78, wherein if the monitored fluid pressure exceeds the predetermined pressure range, then a pumping pressure is reduced by the pump in the closed-loop fluid circuit.

Example 81 includes the method of example 78, wherein if the monitored fluid pressure is below the predetermined pressure range, then a pumping pressure is increased by the pump in the closed-loop fluid circuit and/or additional drug solution or solvent is added to the closed-loop fluid circuit.

Example 82 includes the method of any of examples 76-81, further including terminating the recirculating of a drug solution if a leak in the treatment chamber is indicated by one or more of the following conditions: the fluid pressure in the closed-loop fluid circuit drops below a predetermined minimum pressure; a calculated rate of pressure change in the closed-loop fluid exceeds a predetermined rate of change, and a medical image of the patient shows that one or both of the expandable members is not sufficiently sealing against the wall of the natural lumen.

Example 83 includes the method of example 77, wherein the fluid pressure in the closed-loop fluid circuit is monitored by a pressure sensor mounted on the catheter in the treatment chamber or a pressure sensor located in an electronic console exterior to the patient and in fluid communication with the closed-loop fluid circuit.

Example 84 includes the method of any of examples 59-83, further including flushing the liquid drug from the closed-loop fluid circuit at the end of the treatment session.

Example 85 includes the method of any of examples 76-84, wherein recirculating the liquid drug further comprises pumping the liquid drug solution from the pump through one of the two drug-delivery lumens to the treatment chamber while permitting the liquid drug to return from the treatment chamber to the pump via the other of the two drug-delivery lumens.

Example 86 includes the method of any of examples 59-85, wherein circulating the liquid drug achieves homogeneous concentration of the drug in the liquid drug within in the treatment chamber.

Example 87 includes the method of any of examples 59-86, wherein circulating the liquid drug further comprises continuing to circulate the liquid drug until the drug has saturated the target tissue area and passed therethrough into the surrounding interstitial space or the proximate lymphatic system of the patient, all of which may act as a conduit or reservoir for the drug.

Example 88 includes the method of any of examples 59-87, wherein the expandable member is an elastic balloon and predetermined expansion properties thereof comprise a predetermined relationship between inflation volume and diameter.

Example 89 includes the method of any of examples 59-88, wherein circulating the liquid drug further comprises maintaining a fluid pressure in the treatment chamber below a pre-determined maximum pressure.

Example 90 includes a catheter for delivery of a drug to a target tissue area of an internal body organ of a patient, the catheter having an elongate flexible shaft and an expandable member disposed about a catheter shaft distal region, the expandable member being transformable between a collapsed delivery configuration and an expanded configuration for sealingly engaging a natural lumen extending through the target tissue area to form a closed treatment chamber defined by the portion of the natural lumen distal of the expandable member, the catheter further having first and second drug-delivery lumens extending from a catheter proximal end to respective first and second ports spaced-apart in the shaft region distal of the expandable members.

Example 91 includes the catheter of example 90, wherein the proximal port is located very adjacent the expandable member.

Example 92 includes the catheter of any of examples 90-91, wherein the length between the first and second ports is selectively adjustable to correspond with a length of the target tissue area.

Example 93 includes the catheter of any of examples 90-92, wherein a length of the catheter region distal of the expandable member is selectively adjustable to correspond with a length of the target tissue area.

Example 94 includes the catheter of any of examples 90-93, further including an orientation sensor mounted at the catheter shaft distal region.

Example 95 includes the catheter of any of examples 90-94, wherein the expandable member comprises a compliant balloon inflatable to varying diameters, the catheter further having an inflation lumen extending from the catheter proximal end to the expandable member for inflation thereof.

Example 96 includes the catheter of any of examples 90-95, further including a navigation camera disposed adjacent the distal region.

Example 97 includes the catheter of any of examples 90-96, further including a fiducial marker for referencing the location of the expandable member when the catheter is viewed using an imaging system.

Example 98 includes the catheter of any of examples 90-97, wherein the expandable member is configured for forming a treatment chamber within a lumen of a gastrointestinal tract, a female genital tract, a urinary tract, or a respiratory tract.

Example 99 includes a catheter for local delivery of a drug to a target tissue area of an internal body organ of a patient, the catheter including: an elongate flexible shaft; an expandable member disposed about a distal region of the flexible shaft and being transformable between a collapsed delivery configuration and an expanded configuration for sealing against the wall of a natural lumen extending through the target tissue area to form a treatment chamber defined by the wall of the natural lumen distal of the expandable member; a liquid ingress lumen extending from a shaft proximal end to a liquid ingress port located distal of the expandable member; and a liquid egress lumen extending from a shaft proximal end to a liquid egress port located distal of the expandable member; wherein the functions of the ingress and egress ports are reversible such that either port can be a high point of the formed treatment chamber with respect to gravity.

Example 100 includes the catheter of example 99, further including an orientation sensor mounted at the shaft distal region and operable to indicate to an operator the orientation of the shaft distal region with respect to gravity.

Example 101 includes the catheter of example 100, wherein the orientation sensor is an accelerometer adapted to communicate with an electronic console exterior to the patient.

Example 102 includes the catheter of any of examples 99-101, wherein one of the liquid ingress port and the liquid egress port is located very adjacent the expandable member.

Example 103 includes the catheter of any of examples 99-102, wherein a length of the catheter region distal of the expandable member is selectively adjustable to correspond with a length of the target tissue area.

Example 104 includes the catheter of any of examples 99-103, wherein expandable member is a compliant balloon inflatable to varying diameters, the shaft further having an inflation lumen configured for inflating the compliant balloon.

Example 105 includes the catheter of any of examples 99-104, further including a navigation camera disposed adjacent the distal region.

Example 106 includes the catheter of any of examples 99-105, further including a fiducial marker for referencing the location of the expandable member when the catheter is viewed using a medical imaging system or navigation system.

Example 107 includes the catheter of any of examples 99-106, wherein the expandable member is configured for forming a treatment chamber within a lumen of a gastrointestinal tract, a urinary tract, a female reproductive tract, or a respiratory tract.

Example 108 includes the catheter of any of examples 99-107, further including one or more spaced-apart electrodes disposed distally of the expandable member.

Example 109 includes the catheter of example 108, wherein the electrodes are configured and located to provide an impedance indication when liquid reaches the high point of the formed treatment chamber with respect to gravity.

Example 110 includes the catheter of example 108, wherein the electrodes are configured and located to provide an impedance indication of a concentration of the drug in the drug solution.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be apparent that all hollow organs are eligible for both single and multiple balloon configurations of the devices, systems and methods described herein. It will also be understood that each feature of each embodiment discussed herein, and of each reference cited herein, can be used in combination with the features of any other embodiment.

I claim:

1. A respiratory tract catheter for delivery and evacuation of fluids, the respiratory tract catheter comprising:
   an elongate flexible shaft having only a single expandable member;
   the expandable member is disposed at a distal region of the elongate flexible shaft, the expandable member being transformable between a collapsed delivery configuration and being expanded for creating a sealed treatment chamber distal of the expandable member when engaged with a wall of an airway of a patient;
   an air egress lumen extending from a proximal end of the elongate flexible shaft to an air egress port disposed in the distal region of the elongate flexible shaft, wherein the air egress port is located at a distal end of the expandable member, and is immediately adjacent to the expandable member;
   a liquid flow lumen for delivery of liquid into the sealed treatment chamber, and extending from the proximal end of the elongate flexible shaft to a liquid flow port disposed in the distal region of the elongate flexible shaft, at a location distal to the air egress port,
   wherein the air egress port is configured to facilitate air evacuation when liquid is being delivered into the sealed treatment chamber;
   a reservoir for receiving liquid; and
   a pump fluidly coupled to the reservoir, the air egress lumen, and the liquid flow lumen, wherein the pump, the reservoir, the air egress lumen, and the liquid flow lumen are configured to be fluidly coupled with the sealed treatment chamber to form a closed-loop fluid circuit therewith when the expandable member is engaged with the wall of the airway and the sealed treatment chamber is filled with the liquid, wherein the closed-loop fluid circuit includes a purge port for purging air from the closed-loop fluid circuit.

2. The respiratory tract catheter of claim 1, wherein the expandable member comprises a compliant balloon that is inflatable, the respiratory tract catheter further having an inflation lumen extending from the proximal end of the elongate flexible shaft to the compliant balloon for inflation thereof.

3. The respiratory tract catheter of claim 1, further comprising a navigation camera disposed at the distal region of the elongate flexible shaft.

4. The respiratory tract catheter of claim 1, further comprising a fiducial marker disposed on the expandable member for referencing a location thereof.

5. The respiratory tract catheter of claim 1, wherein the liquid flow lumen is configured to provide at least one of a drug solution, a biologics solution, or a saline solution to flow therethrough.

6. The respiratory tract catheter of claim 1, further comprising a pressure monitor disposed at the distal region of the elongate flexible shaft, wherein the pressure monitor is located at the distal end of the expandable member and disposed in the sealed treatment chamber when the expandable member is engaged with the wall of the airway of the patient.

7. The respiratory tract catheter of claim 1, further comprising an orientation sensor configured to indicate an angle of the respiratory tract catheter with respect to gravity.

8. The respiratory tract catheter of claim 1, further comprising an electrode for detecting liquid, wherein the electrode is disposed distal to the expandable member.

9. The respiratory tract catheter of claim 1, wherein the expandable member, when expanded, has a concave surface adapted to direct air toward the air egress port.

10. The respiratory tract catheter of claim 1, wherein the closed-loop fluid circuit is configured to permit the liquid to circulate through the sealed treatment chamber.

11. A respiratory tract catheter for fluid delivery and evacuation, the respiratory tract catheter comprising:
    an elongate flexible shaft;
    an expandable member disposed at a distal region of the elongate flexible shaft, the expandable member transformable between a collapsed delivery configuration and being expanded for creating a sealed treatment chamber distal of the expandable member when engaged with a wall of an airway of a patient;
    a liquid flow lumen for admission of liquid into the sealed treatment chamber, and extending from a proximal end of the elongate flexible shaft to a liquid flow port disposed in the distal region of the elongate flexible shaft, at a location distal to the expandable member;
    an air egress lumen extending from the proximal end of the elongate flexible shaft to an air egress port disposed in the distal region of the elongate flexible shaft, wherein the air egress port is located such that, when the sealed treatment chamber has a vertical orientation, the air egress port is at a highest point of a portion of the elongate flexible shaft that extends distal of the expandable member within the sealed treatment chamber,
    wherein the air egress port is configured to facilitate air evacuation when liquid is being delivered into the sealed treatment chamber;
    a reservoir for receiving liquid; and
    a pump fluidly coupled to the reservoir, the air egress lumen, and the liquid flow lumen, wherein the pump, the reservoir, the air egress lumen, and the liquid flow lumen are configured to be fluidly coupled with the sealed treatment chamber to form a closed-loop fluid circuit therewith when the expandable member is engaged with the wall of the airway and the sealed treatment chamber is filled with the liquid, wherein the closed-loop fluid circuit includes a purge port for purging air from the closed-loop fluid circuit.

12. The respiratory tract catheter of claim 11, further comprising an orientation sensor configured to indicate an angle of the respiratory tract catheter with respect to gravity.

13. The respiratory tract catheter of claim 11, wherein the expandable member comprises a compliant balloon that is inflatable, the respiratory tract catheter further having an inflation lumen extending from the proximal end of the elongate flexible shaft to the compliant balloon for inflation thereof.

14. The respiratory tract catheter of claim 11, wherein the closed-loop fluid circuit is configured to permit the liquid to circulate through the sealed treatment chamber.

15. The respiratory tract catheter of claim 11, wherein a function of the air egress lumen, and its associated air egress port, and a function of the liquid flow lumen, and its associated liquid flow port, are reversible such that either port is configured to be the highest point with respect to gravity of the portion of the elongate flexible shaft that extends distal of the expandable member within the sealed treatment chamber depending on a position of the patient.

16. The respiratory tract catheter of claim 11, further comprising a pressure monitor disposed at the distal region of the elongate flexible shaft, wherein the pressure monitor is located distal to the expandable member and disposed in the sealed treatment chamber when the expandable member is engaged with the wall of the airway of the patient.

\* \* \* \* \*